United States Patent [19]
Green

[11] 3,972,383
[45] Aug. 3, 1976

[54] SOUND ABSORPTION WITH VARIABLE ACOUSTIC RESISTANCE MEANS BY OSCILLATORY AIR PRESSURE SIGNAL

[75] Inventor: Gary Warner Green, Enfield, Conn.

[73] Assignee: United Technologies Corporation, Hartford, Conn.

[22] Filed: Aug. 1, 1975

[21] Appl. No.: 601,565

Related U.S. Application Data

[63] Continuation-in-part of Ser. No. 481,003, June 19, 1974, abandoned.

[52] U.S. Cl. .................. 181/33 HC; 244/42 CE
[51] Int. Cl.² ............................................ E04B 1/99
[58] Field of Search......... 181/33 H, 33 HB, 33 HC, 181/33 HA, 33 E, 33 G, 51; 415/79, 119; 244/42 CE

[56] References Cited
UNITED STATES PATENTS

| 2,783,008 | 02001957 | .................. 181/33 HB |
|---|---|---|
| 3,294,323 | 12/1966 | Ernst .................. 181/33 HB |
| 3,596,734 | 7/1971 | Yates .................. 181/33 HC |
| 3,820,628 | 6/1974 | Hanson .................. 181/33 HC |

OTHER PUBLICATIONS

"Analytical & Experimental Studies for Predicting Noise Attenuation in Acoustically Treated Ducts for Turbofan Engines"; 1969, E. Feper & L. W. Dean.

Primary Examiner—L. T. Nix
Assistant Examiner—Vit W. Miska
Attorney, Agent, or Firm—John D. Del Ponti

[57] ABSTRACT

A system for varying the acoustic resistance of an acoustical lining disposed in a duct of an air propulsor comprises a nonlinear sound suppression liner having a porous facing sheet overlying a plurality of cells and means for impinging a predetermined oscillatory air pressure signal of 100–160 dB at an inaudible frequency on the facing sheet to vary the acoustic resistance of the facing sheet to make it optimum for a selected sound level and airflow condition in the duct.

6 Claims, 7 Drawing Figures

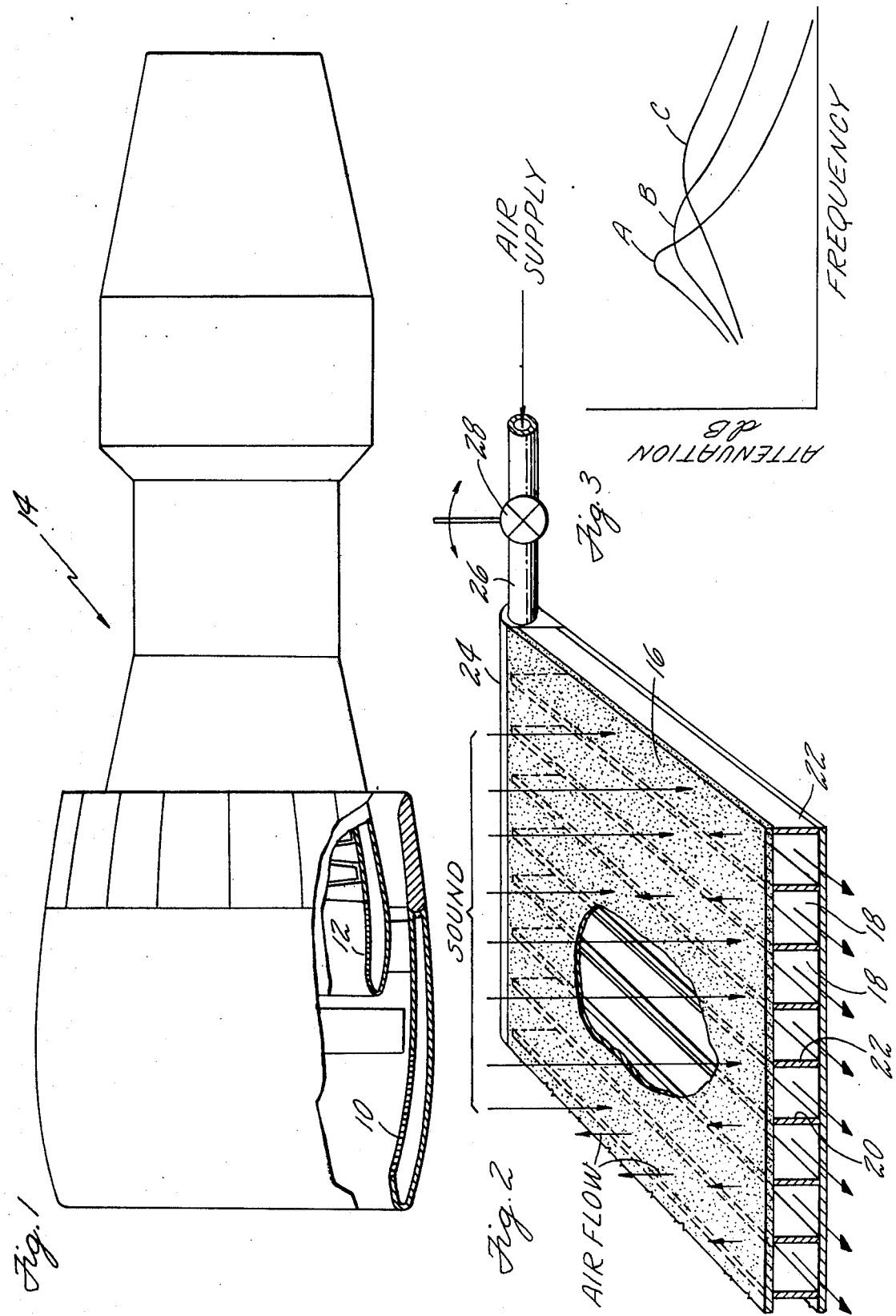

SOUND ABSORPTION WITH VARIABLE ACOUSTIC RESISTANCE MEANS BY OSCILLATORY AIR PRESSURE SIGNAL

BACKGROUND OF THE INVENTION

This is a continuation-in-part application of Ser. No. 481,003 filed June 19, 1974 by the same inventor, now abandoned.

This invention relates to sound absorption systems and more particularly to a system for varying the acoustic resistance of an acoustical lining disposed in an air propulsor duct by providing means for selectively imposing an oscillating flow of fluid, such as air, through the lining.

A typical acoustical panel construction designed for aircraft use is described in U.S. Pat. No. 3,481,427 granted to R. A. Dobbs and R. N. Holmes where a porous sheet overlies a plurality of cavities that are dead-ended by an impervious backing sheet. Accordingly, transmission losses occur by passage of sound waves propagating over the porous surface into still air cavities, resulting in a sound level drop across the porous surface face.

One of the problems extant in optimizing duct lining material for air propulsor ducts centers on the fact that lining material environment during propulsor operation changes dramatically in sound level and grazing flow conditions. These environmental conditions in aircraft engine and APU inlet and exhaust ducts, for example, change significantly for different air flight modes, e.g., takeoff, cutback and approach and APU operating power levels.

SUMMARY OF THE INVENTION

It is an object of this invention to maximize the attenuation of sound by varying the acoustic resistivity of nonlinear duct acoustical linings to optimize lining resistance throughout the range of changing conditions encountered thereby.

The present invention contemplates a system for adjusting the noise absorption quality of an acoustical lining by changing its acoustic properties so that its resistance will be optimum for the sound level and grazing flow conditions encountered by providing means for imposing a selected oscillating air pressure signal on the lining material.

In accordance with the present invention, a system for varying the acoustic resistance of an acoustical lining disposed in an air propulsor duct comprises a nonlinear sound suppression liner having a porous facing sheet and a substantially close-ended, side and bottom enclosure member defining a cavity and having an open top surface, the facing sheet extending over said top surface and a plurality of sidewalls extending between the facing sheet and the enclosure member in the cavity to divide the cavity into a plurality of cells and means for superimposing an oscillatory high level pressure signal on the aforesaid facing sheet to vary the acoustic resistance thereof to make it linear for a selected sound level and grazing airflow condition in the duct. The pressure signal is at a level of 100–160 dB and at a frequency which is inaudible to the human ear, i.e., either above 20 kHz or below 20 Hz. The oscillatory pressure signal may be provided externally by a duct-mounted horn driver, high frequency siren or the like or internally by a manifolded control valve supplied by pressurized air either at a single pressure or at two different pressures. The duct lining may be constructed from a porous sheet overlying either channel or cellular sound absorption cavities dead-ended by an impervious hard back wall. For internally supplied oscillating pressure, apertures are formed in the hard back wall and/or adjacent channels and/or slots in the cell walls.

Some of the advantages of the present invention are:
1. Changes in liner acoustic resistance because of contamination of the duct lining due to dirt, oil, etc., may be compensated for by varying the oscillatory signal level.
2. For applications for which the optimum acoustic properties are not too well known, they can be empirically determined after installation by varying the oscillatory signal until a maximum attenuation is achieved.
3. If the major variations exist between units of the same design, they may be individually optimized by using different oscillatory signal levels.

BRIEF DESCRIPTION OF THE DRAWINGS

An understanding of the invention will become more apparent to those skilled in the art by reference to the following detailed description when viewed in light of the accompanying drawings, wherein:

FIG. 1 is an elevation view partly in section showing the lining in the duct of the inlet of a ducted fan and compressor section of a power plant;

FIG. 2 is an exploded perspective view partly in schematic illustrating an acoustical panel configuration;

FIG. 3 is a graph plotting attenuation in decibels (dB) vs. frequency illustrating the effect of this invention;

DESCRIPTION OF THE PREFERRED EMBODIMENT

Figure 4:
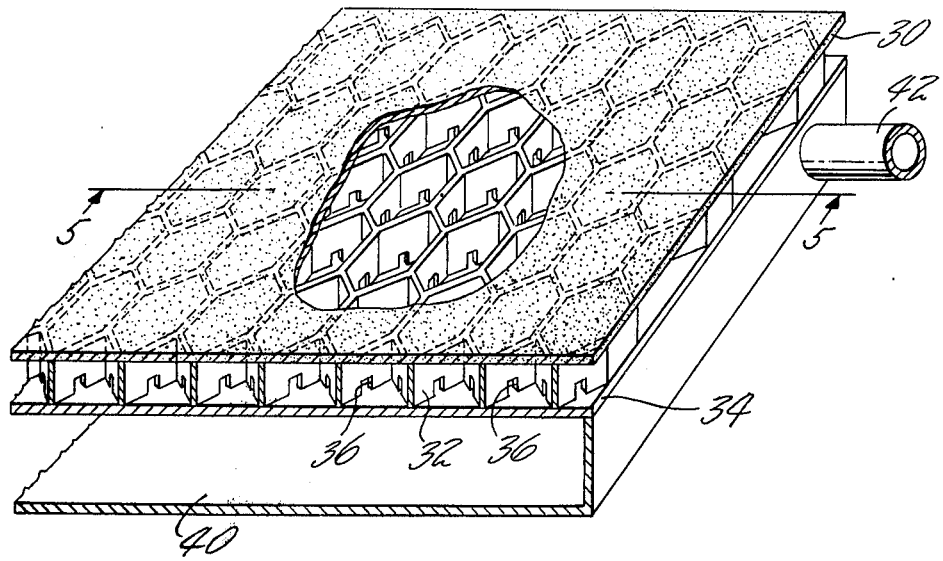
FIG. 4 is an exploded perspective view illustrating another acoustical panel configuration.

It will be helpful to the understanding of the present invention to appreciate, by reference to FIGS. 1, 2 and 4, the related inventive concept described in copending application Ser. No. 597,630 (Project H260A) by G. Green and E. Feder which was mailed to the U.S. Patent Office on July 18, 1975 and is assigned to the same assignee as the present invention.

As noted from FIG. 1 the linings 10 and 12 are in the inlet of the fan and compressor section of a propulsor generally illustrated by numeral 14 and are merely exemplary of locations for applying the lining material. As will be appreciated, the particular location of the lining is not important to this invention as the invention has contemplated use in any location where environmental conditions change, be it at the inlet or exhaust of an engine, ducted fan or auxiliary power unit.

Referring to FIG. 2, the lining 10 and 12 is shown as comprising a nonlinear porous sheet 16 overlying open-ended channel cells 18 defined by adjacent, axially extending spaced walls 20 radiating from the nonporous hard back wall 22. As will be appreciated by those skilled in the art, porous sheets include metallic and nonmetallic plates with various kinds of perforations as well as fine meshes of woven metallic and nonmetallic fibers. One end of the channels 18 may be blocked off by an end plate or may be abutted against the wall of the structure to which it is mounted. As described in the aforesaid application, a manifold or header 24 is mounted on the other end and serves to distribute a steady flow of air to all of the channels. An air feed line 26 feeds air to header 24 and valve 28 regulates the flow thereto. Obviously valve 28 may be manually adjusted and/or may automatically respond to any signal indicative of aircraft flight conditions as, for example, power lever position, airflow, etc. Suffice it to say that the purpose of the valve 28 is to regulate the airflow through the liner so as to achieve the desired sound attenuation characteristics.

It should be noted that the primary concept described in the related application centers on bringing the lining material, by means of a steady airflow therethrough, to a condition of linearity. Lining material is linear when the air velocity through the material is directly proportional to the pressure drop thereacross. Lining material is nonlinear when the aforesaid relationship between air velocity and pressure drop is some function, e.g., a square or other function other than directly proportional.

In essence, the quantity of air from the air supply flowing through the channels 18 and passing through the porous sheet 16 serves to tune the lining for a given condition i.e., to optimize its resistance for maximum effective sound absorption. It has been found that a change in the flow and sound level in the duct (otherwise referred to as grazing flow) will vary the attenuation spectrum as is shown in FIG. 3. Curves A, B and C illustrate the attenuation spectrum for three different duct flow conditions in an exhaust duct — i.e., Curve A represents takeoff conditions which include high velocity grazing airflow, B, cutback conditions which include medium velocity grazing airflow, and C, approach conditions at approach which include low velocity grazing airflow. For each condition, there is an optimum resistance which will produce maximum noise reduction. According to the related application, the resistance of the lining may be made to behave as shown in Curve D, D' and D'' in FIG. 7 when the steady thru-flow of air from the air supply is adjusted to set the desired flow resistance over the range illustrated for each condition encountered. Thus, the attenuation spectrum of Curve A, FIG. 3, will have a flow resistance illustrated by Curve D, Curve B by D' and Curve C by D''. Curve E is exemplary of a prior art liner having a different porosity and not having its acoustic resistance adjustable as taught in the related application or as taught herein, and shows that this characteristic is nonlinear.

Figure 5:
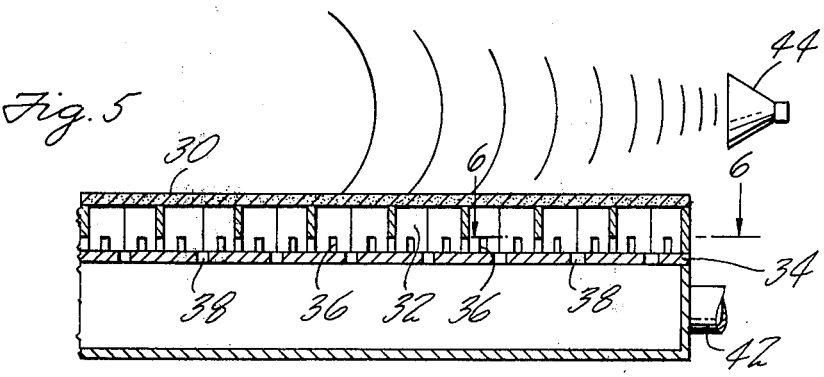
FIG. 5 is a section taken along line 5—5 of FIG. 4 showing the presence of a horn driver.
Figure 7:
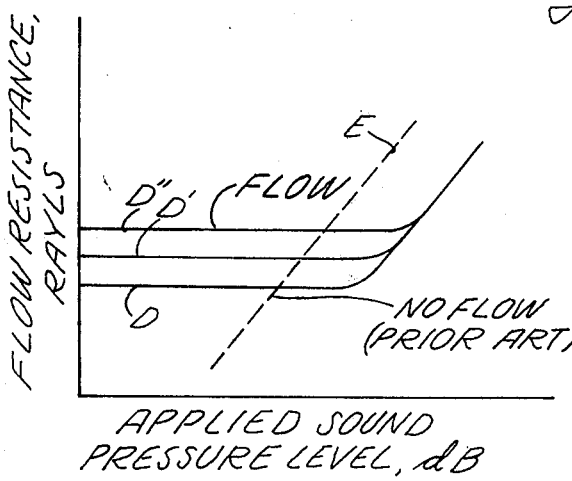
FIG. 7 is a graph showing the linearity of facing materials with and without flow plotted on log-log scale.
Figure 6:
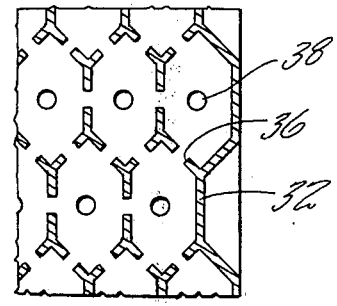
FIG. 6 is a section taken along line 6—6 of FIG. 5.

It has also been found that the resistance of the lining will be made to behave as shown in Curve D, D' and D'' in FIG. 7 when an oscillatory pressure signal of 100–160 dB (reference is $2 \times 10^{-4}$ dynes per square centimeter) at an inaudible frequency is impinged on the facing sheet. Thus, for duct lining environmental conditions which require increasing the acoustic resistance and/or very linear characteristics, an oscillatory pressure signal of relatively high sound pressure level (e.g., 125–160 dB) is imposed on the facing sheets. For duct environmental conditions requiring a smaller acoustic resistance, etc., a signal of lesser sound pressure level (e.g., 100–125 dB) is imposed thereon. By controlling the produced oscillatory pressure level and frequency, the duct lining material may be optimized for any environmental conditions, the oscillatory pressure being a constant for the selected acoustic resistance and the resistance being changeable by varying the oscillating pressure signal during flight. FIGS. 4, 5 and 6 illustrate another acoustical panel construction having a plurality of honeycomb acoustical or resonating cells which may be utilized in combination either with header and low frequency (below audible) oscillatory air pressure signal generating means to adjust resistance or with a high frequency (above audible) horn driver or siren. The porous sheet 30 overlies the honeycomb core 32 and a hard wall 34 is mounted on the back face. The honeycomb core consists of a network of sidewalls 35 as is known in the art. Typically, the sidewall network forms a plurality of identically shaped cells — in this case the cells are of hexagonal configuration. Apertures 38 are formed in wall 34 located so as to communicate with a selected number of the cells. A plurality of slots 36 are preferably formed on each of the sidewalls or back face of honeycomb core 32. Header 40 is mounted on the face of wall 34 and like header 24 serves to distribute the oscillatory air pressure signal to each of the cells through apertures 38 to the porous sheet. In order to achieve variable acoustic resistance/high linearity linings according to the present invention, the oscillatory pressure signal must be imposed on the facing sheet. Thus as shown in FIG. 5, the horn driver 44 is mounted adjacent to or in proximity of the facing sheet. The horn driver generates pressure waves for oscillating the thru-flow in and out of the facing sheet and may be mounted on either face, i.e., bottom or top, of the facing sheet 30. In this embodiment the header 40 and its inlet pipe 42 could be eliminated. Of course, as indicated, the header system may be utilized to distribute pressure signals below the audible range. The header 24, pipe 26 and valve 28 of the FIG. 1 embodiment, or the header 40 of the FIGS. 4 and 5 embodiment, may, for example, be utilized to supply alternate pulses of air at different pressures or even sequential pulses of air at a single pressure so long as the frequency is below 20 Hz and the oscillating pressure level is 100–160 dB. As will be appreciated, any means for generating an oscillating flow (biasing flow) through the facing sheet is contemplated by this invention. In lieu of a horn driver, for example, a high frequency siren or an internal, manifolded, two way control valve supplied by air at two different pressures may be utilized. As indicated, an applied acoustic signal can change the acoustic resistance of the lining material. It will be noted, however, that when used in a duct, any bends will quickly attenuate very high frequency biasing signals and impair their usefulness. Very low frequency oscillations will, however, pass around such bends with less attenuation of the pressure level.

The operation of the above concept may best be illustrated by the following example. For a duct environment wherein (1) at approach the noise sound level is 145 dB and the grazing airflow is 300 ft/sec and (2) at takeoff the noise sound level is 155 dB and the grazing airflow is 500 ft/sec, it was determined that optimum flow resistance, in order to attain maximum attenuation, is provided by a lining material having a flow resistance of 40 rayls during approach and by a liner providing a flow resistance of 48 rayls during takeoff. Therefore, for approach, there exists an optimum resistance which is different than for takeoff. A nonlinear liner comprising a hard wall backing, a layer of 0.75 inch deep, 0.75 inch honeycomb cells and either a perforated plate facing having 12 percent open area during approach or a perforated plate having 18 percent open area during takeoff, will provide the aforesaid optimum flow resistances. By following the teachings of the present invention, it will be appreciated that a single liner may be provided to obtain a plurality of attenuation maxima. For example, the liner having 18 percent open area may be utilized with no externally oscillatory pressure signal supplied by the horn driver during takeoff so that the optimum flow resistance of 48 rayls and hence the maximum attenuation during that condition will obtain. During approach however, the oscillatory signal from the horn driver is effected in an amount to render the same 18 percent open area liner to have a flow resistance of only 40 rayls.

It should be understood that the invention is not limited to the particular embodiments shown and described herein, but that various changes and modifications may be made without departing from the spirit or scope of this novel concept as defined by the following claims.

I claim:

1. A system for varying the acoustic resistance of an acoustical lining disposed in a duct of an air propulsor subject to changing sound level and grazing airflow conditions in said duct comprising:
   a nonlinear sound suppression liner having a porous facing sheet and a substantially close-ended side and bottom enclosure member defining a cavity and having an open top surface, said facing sheet extending over said top surface and a plurality of sidewalls extending between said facing sheet and said enclosure member in said cavity to divide said cavity into a plurality of cells; and
   means adjacent said facing sheet for impinging an oscillatory pressure signal of 100–160 dB at an inaudible frequency on said facing sheet to vary the acoustic resistance thereof to a maximum for a selected sound level and airflow condition in the duct.

2. The system of claim 1 wherein said signal is above 20 kHz.

3. The system of claim 1 wherein said sidewalls form cells in the form of channels.

4. The system of claim 1 wherein said sidewalls form cells in the form of a honeycomb.

5. The system of claim 4 wherein said sidewalls include openings formed between adjacent cells.

6. A method for varying the acoustic resistance of a nonlinear acoustical lining having a porous facing sheet and a substantially close-ended, side and bottom enclosure member defining a cavity having a plurality of cells, said lining being disposed in a duct of an air propulsor subject to changing sound level and grazing airflow conditions comprising:
   mounting adjacent said facing sheet means for producing an oscillatory pressure signal of 100–160 dB at an inaudible frequency; and
   impinging said oscillatory signal on said facing sheet to change the acoustic resistance of said liner to an acoustic resistance which is optimum for the sound level and grazing airflow condition in the duct.

* * * * *